United States Patent [19]
Campbell et al.

[11] Patent Number: 5,954,709
[45] Date of Patent: Sep. 21, 1999

[54] LOW PROFILE INTRODUCER AND ROTATOR

[75] Inventors: Louis A. Campbell; Jeffrey M. Mabrey; Christopher A. Heinrich, all of Austin, Tex.

[73] Assignee: Sulzer Carbomedics Inc., Austin, Tex.

[21] Appl. No.: 08/851,572

[22] Filed: May 5, 1997

[51] Int. Cl.[6] ........................................ A61B 7/00
[52] U.S. Cl. ........................................ 606/1; 623/2
[58] Field of Search ............... 606/1, 108, 99; 623/2, 900, 66; 206/438

[56] References Cited

U.S. PATENT DOCUMENTS

| | | | |
|---|---|---|---|
| 4,585,453 | 4/1986 | Martin | 623/2 |
| 4,683,883 | 8/1987 | Martin | 606/1 |
| 5,236,450 | 8/1993 | Scott | 623/2 |
| 5,443,502 | 8/1995 | Caudillo et al. | 623/2 |
| 5,480,425 | 1/1996 | Ogilive | 623/2 |
| 5,531,785 | 7/1996 | Love et al. | 623/2 |
| 5,578,076 | 11/1996 | Krueger et al. | 606/1 |
| 5,582,607 | 12/1996 | Lackman | 623/2 |
| 5,713,951 | 2/1998 | Garrison et al. | 623/2 |
| 5,713,952 | 2/1998 | Vanney et al. | 623/2 |

*Primary Examiner*—Linda C. M. Dvorak
*Assistant Examiner*—Bryan K. Yarnell
*Attorney, Agent, or Firm*—Philip S. Lyren; Kenneth S. Barrow

[57] ABSTRACT

A device for positioning during surgery, a heart valve prosthesis having a general annular configuration with an inside diameter that includes a handle and a introducer/rotator. The handle has a proximal end and a distal end. The introducer/rotator is attached to the distal end of the handle and has a length in operative relates to the inside diameter of the valve prosthesis. The introducer/rotator has a width that is less than the length, which facilitates intercostal insertion through a patient's ribs.

22 Claims, 4 Drawing Sheets

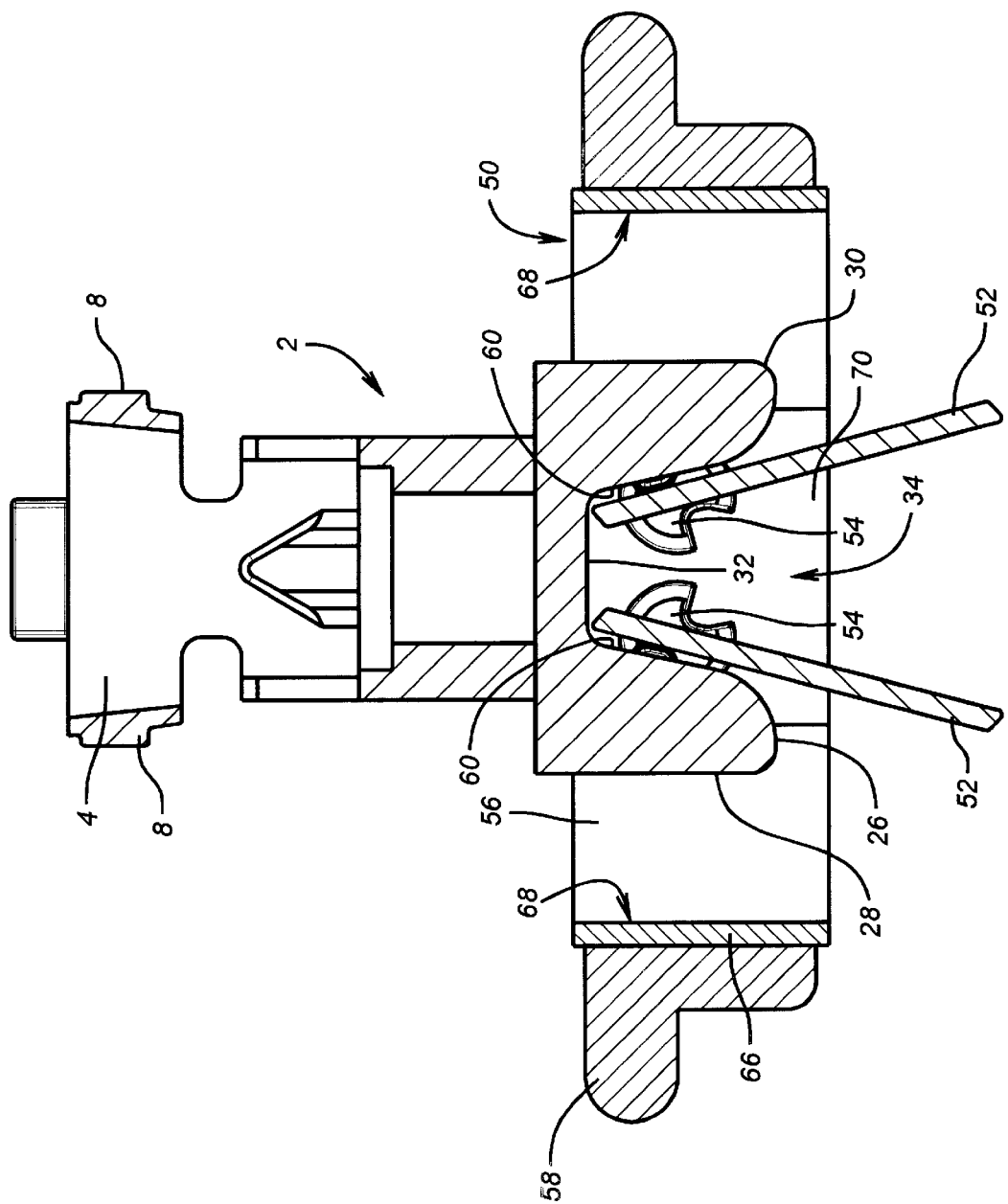

LOW PROFILE INTRODUCER AND ROTATOR

BACKGROUND

The present invention relates to a low profile instrument for introducing and rotating a prosthetic heart valve during implantation.

Holders for positioning heart valve prosthesis are used for positioning (i.e., holding, supporting and rotating) prosthetic heart valves during surgery. Often heart valve replacement surgery includes a median sternotomy or a large left thoracotomy to gain unobstructed access into a patient's thoratic cavity. Such procedures allow the surgeon to see the patient's heart more directly, and to have more direct instrument access for: (1) excising the natural valve tissue; (2) introducing a heart valve prosthesis into the patient's natural valve annulus; (3) securing the prosthetic valve into position; and (4) rotating the orifice and leaflet assembly of the prosthesis to minimize interference with the heart's subannular anatomy. However, these invasive, open-chest procedures produce a high degree of trauma, a significant risk of complications, extended hospital stay, and a painful recovery period for the patient.

Recently, less invasive cardiac surgery techniques have been developed where an open-heart surgery is performed through small incisions between two ribs. This small intercostal thoracotomy is performed instead of a median sternotomy or other form of gross thoracotomy, substantially reducing the above-mentioned trauma, risk of complication, recovery time, or pain for the patient. However, when performing this procedure, care must be taken not to spread the ribs too far. Some surgeons have recently indicated that a thoracotomy incision should not be spread greater than 15 millimeters for an intercostal insertion since deflecting the ribs to a greater dimension can result in significant pain for the patient. The nerve under the rib can be crushed and damaged if the intercostal incision is spread beyond the 15 millimeters.

Therefore, the devices and instruments for performing percutaneous penetrations within these intercostal spaces for less-invasive heart or great vessel surgery must be simple and have "low profile". Currently marketed rotators and valve holders are too bulky to fit through this intercostal space without spreading the patient's ribs too far, and are more complicated than necessary to simply and reliably percutaneously introduce and rotate a prosthetic valve during implantation.

SUMMARY OF THE INVENTION

The invention provides for a device for engaging a heart valve prosthesis during implantation and includes a handle and low profile introducer/rotator. An advantage of the introducer/rotator is that, when engaged with the valve prosthesis, the length of the rotator is in operative relation with the inside diameter of the valve annulus, and the width of the introducer is less than that diameter. The introducer/rotator is rigidly connected to, and easily engaged with, a reusable endoscopic instrument handle, avoiding cost associating with more complex (i.e., non-rigidly connected such as a holder that changes relational position with the handle) valve handles or introducers.

Another advantage is that the introducer/rotator passes through a small percutaneous intercostal incision avoiding the need to spread the ribs which would result in pain or injury to the patient. The valve introducer/rotator easily engages the heart valve prosthesis through self-aligning surfaces, and provides for positioning the valve axially via an axial contact surface that is parallel to the plane of valve annulus, and positioning the valve radially via a radial contact surface that is transverse to such plane. The introducer rotator has the advantage of providing these positioning forces to rotate the orifice and leaflets assembly of the valve with a protective groove, which protects the leaflets and other parts of the valve from structural damage. An understanding of these and other advantages and features of the invention is described below.

DETAILED DESCRIPTION OF THE PREFERRED EMBODIMENT

Drawings:

FIG. 6 is a cross-sectional view of the valve holder introducer/rotator of FIG. 3 connected to a heart valve prosthesis.

STRUCTURE AND OPERATION

Figure 2:
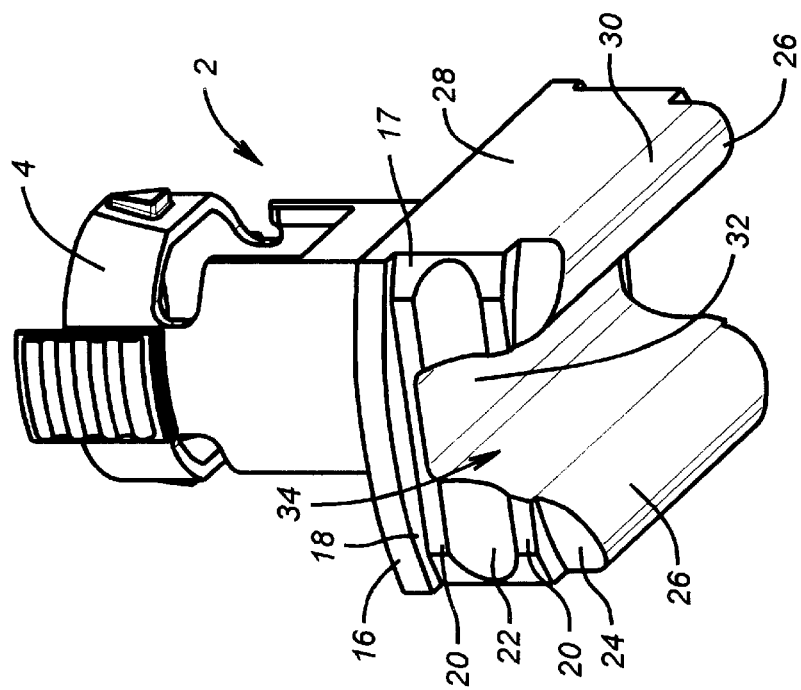
FIG. 2 is a bottom side perspective view of the low profile introducer/rotator in FIG. 1.

Referring to FIGS. 1–6, prosthetic valve introducer/rotator 2 includes a handle engaging end 4 which is designed to be releasably connected to the shaft of a handle (not shown). Alignment indicator 6 marks the position for the user to introduce the handle into engaging end 4. A similar indicator exists on the distal of the handle (not shown), so that the user simply lines up the indicators in order to put the instrument together. In this particular embodiment, finger tabs 8 are provided to release the handle from engaging end 4. Engaging end 4 provides a snap fit with the distal end of the handle (not shown), with the distal tip of the handle resting in engagement recess 10 when the handle and introducer/rotator 10 are connected. Engagement recess 10 is shown as a smooth recess so that the distal end of the handle slip-fits into recess 10. Also provided in the engaging end is self-guiding groove 12 which allows the distal end of the handle to be correctly positioned for coupling with rotator 2. For simplicity of operation and cost-efficient manufacture, the connection between the handle and introducer/rotator 2 is rigid; i.e., the rotator cannot pivot or reorient for introduction through the intercostal space of a patient's ribs. Radii 14 are provided so that the low profile rotator is more easily cleaned. Referring to the FIG. 6, a heart valve prosthesis 50 is shown in cross-section, attached to introducer/rotator 2. The prostheses 50 generally includes annular valve body 66 with an interior surface 68. Surface 68 has a right circular cylindrical shape for a major portion of its length, but is interrupted by a pair of diametrically opposed flat sections 70 (as FIG. 6 is a cross-section, only one flat section 70 is shown). The distance between flat section 70 defines the smallest internal diameter of the annulus 56 of prothesis 50. The annulus 56 is the central passageway through which blood flows, and contains leaflets 52 that swing or rotate about pivots 54. Pivots 54 reside in the flat section 70 of prosthesis 50. Surrounding annulus 56 is sewing ring 58 which provides means for the surgeon to attach prosthesis 50 to the patients natural valve annulus.

Figure 1:
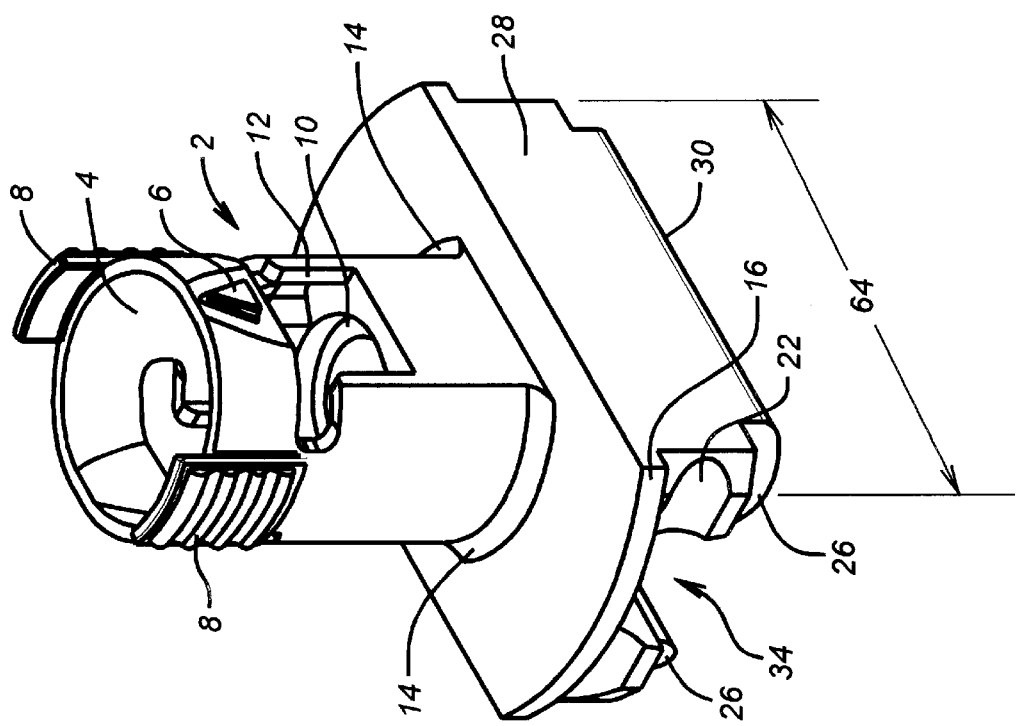
FIG. 1 is a topside perspective view of a low profile introducer/rotator in accordance with our invention.
Figure 3:
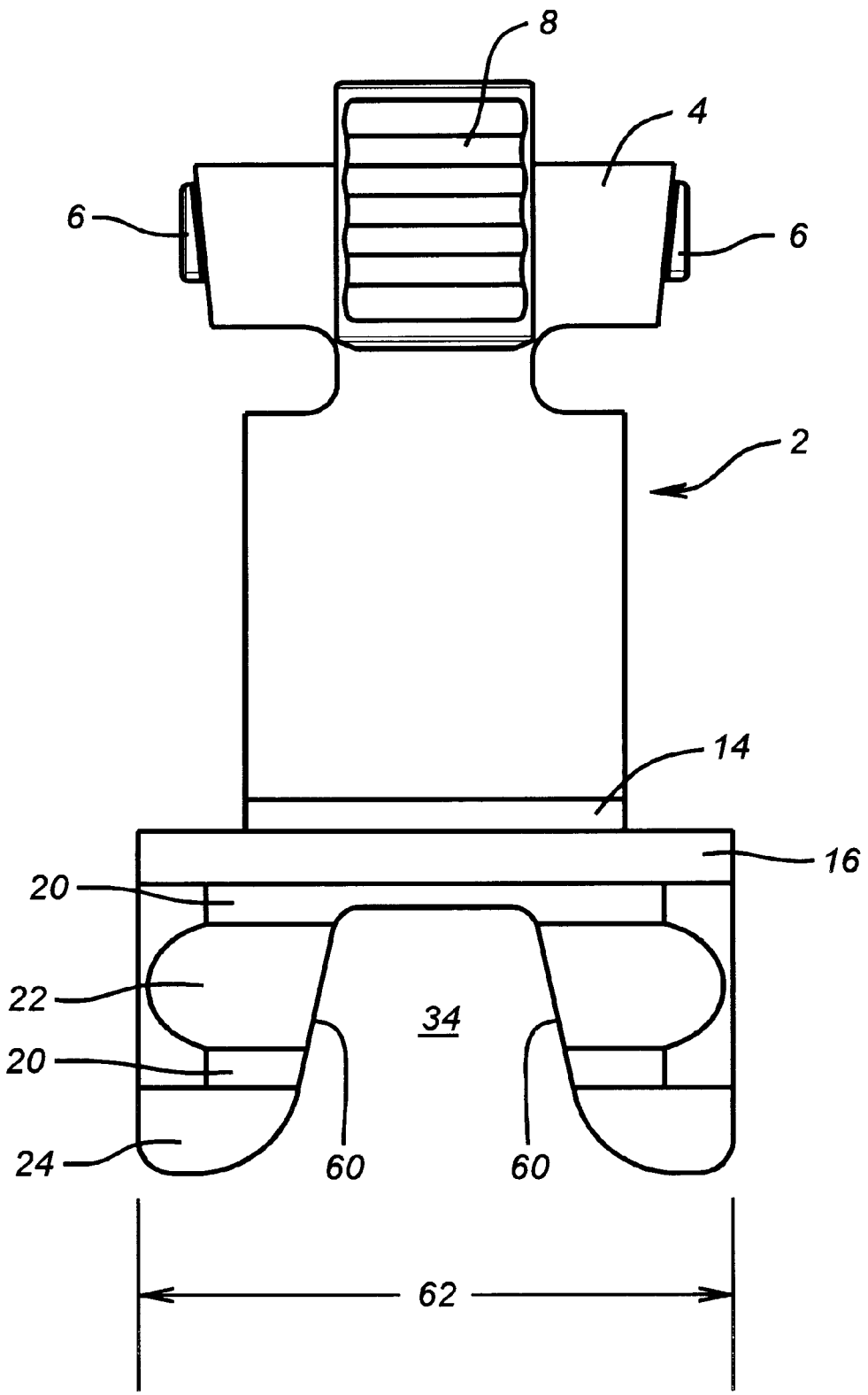
FIG. 3 is a width side view of the low profile introducer/rotator.
Figure 4:
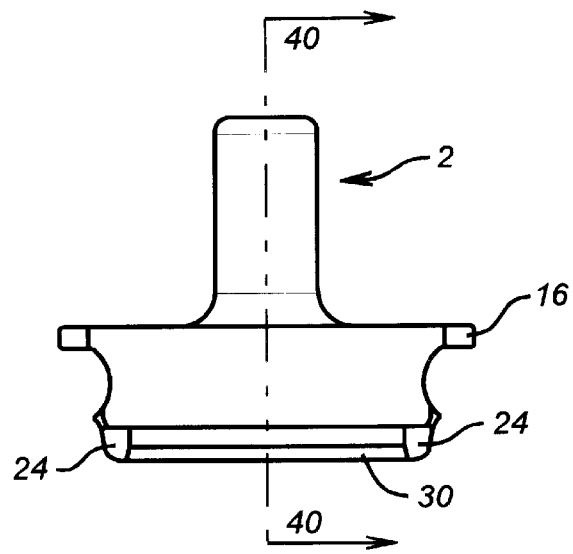
FIG. 4 is the length side plan view of the low profile introducer/rotator.
Figure 5:
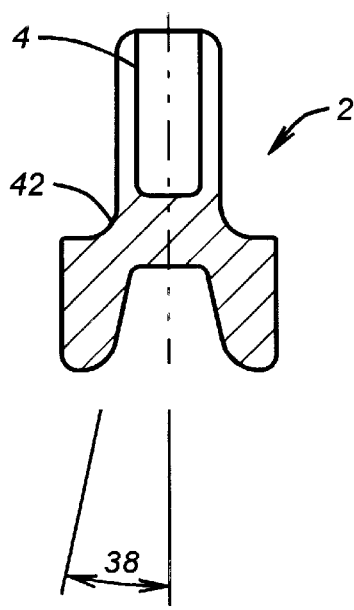
FIG. 5 is a cross-sectional view of the valve introducer/rotator taken a long line 40—40.

As shown in FIG. 1, introducer/rotator 2 has a length 64 designed to fit between flat section 70 of the heart valve prostheses when engaged with the valve. This operative relation between length 64 and the inside diameter of annulus 56 allows the introducer/rotator to position the valve while the leaflets are protected.

In this particular embodiment, of FIGS. 1–6 the low profile introducer and rotator is composed of a series of coaxial cylinders which are truncated resulting in a width 62 small enough to pass through the intercostal spaces of the patient's ribcage, without significantly displacing any of the patient's ribs. In this embodiment, the width 62 of the cylinders are truncated to 14 millimeters. The restriction on width 62 always results in a low-profile rotator with a length to width ratio of greater than 1. Of course, the ratio is not significant, so long as the width 62 is less than length 64, and therefore is less than the inside diameter of the prosthetic heart valve.

Outside cylinder 16 acts as a stop for the introducer rotator when it contacts the inflow edge of the orifice of the prosthetic heart valve, therefore, preventing the leaflets from bearing any axial load. Engaging surface 18 of outside cylinder 16 is a surface that rests against the prosthetic heart valve and provides for axial engagement. Engagement flat 20 is a surface that engages the flat portion of the orifice of the prosthetic heart valve and provides rotational force for positioning the valve. Flat 20 is formed from an intermediate cylinder 17, and induces the rotation of the orifice and leaflets assembly. Flat 20 is formed by truncating cylinder 17 once more, the additional truncation occurring in 90 degrees from the truncation at intercostal release surface 28. This engagement flat 20 allows the introducer/rotator to match the opposing flat surfaces 70 of the valve internal diameter.

Proximal to this truncation (surface 28) is a notch 22 that aids in directing the introducer in the axial position. Notch 22 also helps guide the introducer/rotator into correct alignment for full engagement into the orifice and leaflets assembly when presented at an angle to the assembly's central axis. The cylinder formed at surface 24 is slightly less than the distance between the orifice flats 70 and will engage the valve for radial alignment. This cylinder is smaller than the orifice flats 70 so the introducer/rotator will be held in radial alignment with the valve while it is rotationally being aligned. Cylinder surface 24 allows the introducer/rotator to rotate freely on the leaflets inflow edge which helps guide the introducer/rotator 2 into the correct rotational alignment for full engagement into the orifice and leaflets assembly. Surface 26 is also a relieved surface to prevent excessive pressure from being applied to the leaflets. Relieved surfaces 32, 60, and 26 define leaflet groove 34 and protects the leaflets from rotational or axial pressure that may result in damage to the valve. Indeed, as shown in the embodiment in FIG. 6, groove 34 surrounds leaflets 52 while the leaflets are in the open position, but does not exert pressure on, or necessarily touch the valve leaflets 52 during rotation of the valve. Intercostal relieved surface 28 provides the low profile character of this introducer rotator so that it can be easily inserted between the patient's ribs. Much of the construction of this embodiment contains rounded surfaces such as rounded surface 30 to limit possible damage to the heart valve and to provide for easier cleaning and molding. Relief angle 38 is designed to prevent surface 60 from having contact with leaflets 52. In the embodiment shown in FIG. 6, surfaces 60 are substantially parallel to leaflets 52 in the fully open position.

Other embodiments are within the scope of the following claims.

We claim:

1. A heart valve holding device for holding a heart valve prosthesis having an annular configuration with an inside diameter, said device comprising:

an introducer/rotator for holding a heart valve prosthesis and for coupling to a distal end of a handle having a length sized for holding an inside diameter of heart valve, a width sized for holding an inside diameter of heart valve, and a height, wherein said length is sized approximately equal to an inside diameter and said width is substantially less than an inside diameter, and wherein said introducer rotator has a rectangular configuration, wherein two parallel and flat surfaces extend substantially along said length and two other parallel and generally flat surfaces extend substantially along said width.

2. The device of claim 1 in which said width is about 14 mm.

3. The device of claim 1 in which said flat surfaces along said width are capable of engaging an inside diameter for holding a heart valve prosthesis.

4. The device of claim 1 in which said flat surfaces along said width further include a notch.

5. The device of claim 4 in which said notch is configured as a groove and extends substantially along an entire length of said width.

6. The device of claim 1 in which said rectangular configuration includes two cylindrically shaped bodies that extend parallel to each other along said length.

7. The device of claim 6 in which said rectangular configuration further includes a groove that extends between said bodies and along said length.

8. The device of claim 1 in which said width is capable of fitting through an intercostal space between a patient's ribs.

9. The device of claim 1 in which:

a heart valve prosthesis has an annulus defining a plane; and said introducer/rotator further comprises an axial contact surface parallel to said plane, and a radial contact surface transverse to said plane for engagement with a heart valve prosthesis.

10. The device of claim 1 in which a ratio of said length to said width is greater than 1.

11. The device of claim 1 in which:

a heart valve prosthesis further comprises leaflet occluders capable of rotating from an open position to a closed position and rotatably attached to a flat surface along an inside diameter; and said introducer/rotator further comprises a protective groove capable of holding said occluders.

12. The device of claim 11 in which said groove is capable of maintaining said occluders in an open position.

13. A heart valve holding device for holding a heart valve prosthesis having an annular configuration with an inside diameter, said device comprising:

an introducer/rotator for holding a heart valve prosthesis and for coupling to a distal end of a handle having a generally rectangular configuration with a length, a width, and a height, wherein said rectangular configuration comprises two parallel and flat surfaces extending substantially alone said length and two other parallel and generally flat surfaces extending substantially along said width.

14. The device of claim 13 in which said length and said width are sized to extend between an inside diameter of a heart valve prothesis.

15. The device of claim 14 in which said length extends substantially an entire distance between an inside diameter, and said width extends a distance substantially less than said length.

16. The device of claim 15 in which said width is about 14 mm.

17. The device of claim 13 in which said width is substantially less than said length.

18. The device of claim 13 in which a ratio of said length to said width is greater than 1.

19. The device of claim 13 in which said flat surfaces along said width are capable of engaging an inside diameter for holding a heart valve prosthesis.

20. The device of claim 13 in which said introducer/rotator further comprises an engaging surface along said width, said surface capable of applying rotational force to a heart valve.

21. The device of claim 20 in which said introducer/rotator further comprises a protective groove capable of engaging with a pair of leaflets on a heart valve prosthesis and capable of maintaining leaflets in an open position.

22. The device of claim 21 in which said groove extends along said length and is formed between two substantially rectangular bodies.

* * * * *